United States Patent
Wang et al.

(10) Patent No.: US 10,982,015 B2
(45) Date of Patent: Apr. 20, 2021

(54) PEG-ACS/M-SIRNA NANOCOMPOSITE, APPLICATION THEREOF, AND METHOD FOR REDUCING HISTAMINE CONTENT DURING FISHMEAL STORAGE

(71) Applicants: Zhejiang Gongshang University, Hangzhou (CN); Rongcheng Huatong Marine Biotechnology Co. LTD, Rongcheng (CN)

(72) Inventors: Yanbo Wang, Hangzhou (CN); Linglin Fu, Hangzhou (CN); Zhongfu Liu, Rongcheng (CN); Feifei Wang, Hangzhou (CN); Fan Li, Hangzhou (CN); Junbo Liang, Rongcheng (CN)

(73) Assignees: ZHEJIANG GONGSHANG UNIVERSITY, Hangzhou (CN); RONGCHENG HUATONG MARINE BIOTECHNOLOGY CO. LTD., Rongcheng (CN)

(*) Notice: Subject to any disclaimer, the term of this patent is extended or adjusted under 35 U.S.C. 154(b) by 73 days.

(21) Appl. No.: 16/133,716

(22) Filed: Sep. 18, 2018

(65) Prior Publication Data
US 2020/0010574 A1 Jan. 9, 2020

(30) Foreign Application Priority Data
Jul. 6, 2018 (CN) .......................... 201810739772.5

(51) Int. Cl.
*C12N 15/11* (2006.01)
*A61K 48/00* (2006.01)
(Continued)

(52) U.S. Cl.
CPC ........... *C08B 37/003* (2013.01); *C07H 21/02* (2013.01); *C12N 15/52* (2013.01); *B82Y 30/00* (2013.01);
(Continued)

(58) Field of Classification Search
CPC ...... C08B 37/003; C07H 21/02; C12N 15/52; C12N 15/113; C12N 15/1137; B82Y 30/00; A61K 47/60; A61K 47/549
See application file for complete search history.

(56) References Cited

FOREIGN PATENT DOCUMENTS

WO WO-2012094115 A1 * 7/2012 ......... A61K 31/7088

OTHER PUBLICATIONS

Nitta et al. (Journal of Food Protection, 2016 vol. 79:463-467).*
Costa et al. (PLoS One, 2013, e70072 vol. 8:pp. 1-13).*
Ragelle et al. (Methods Mol. Biol. 2016, vol. 1364:143-50).*

* cited by examiner

*Primary Examiner* — Terra C Gibbs
(74) *Attorney, Agent, or Firm* — Bayramoglu Law Offices LLC (57) ABSTRACT

The present invention provides a PEG-ACS/M-siRNA nanocomposite application, and method for reducing the histamine content during fishmeal storage thereof. A small interfering ribonucleic acid (siRNA) is designed and prepared according to a histidine decarboxylase gene of *Morganella morganii* (*Morganella morganii* subsp. *morganii* KT), and the histidine decarboxylase gene has a sequence of SEQ ID No: 1. A PEG-ACS/M-siRNA nanocomposite is prepared by using a PEGylated arginine-modified chitosan as a carrier. A PEG-ACS/M-siRNA nanocomposite is added to fishmeal in a certain ratio. The method for reducing the histamine content during fishmeal storage has a significant inhibitory effect on the histamine content during fishmeal storage, and can reduce the histamine content in fishmeal by 49%-53%, which has great significance for the control of biogenic amines in fishmeal in the feed industry.

20 Claims, 3 Drawing Sheets
Specification includes a Sequence Listing.

(51) Int. Cl.
  *C07H 21/02* (2006.01)
  *C07H 21/04* (2006.01)
  *C08B 37/08* (2006.01)
  *C12N 15/52* (2006.01)
  *B82Y 30/00* (2011.01)
(52) U.S. Cl.
  CPC .................. *C12N 2310/351* (2013.01); *C12Y 401/01022* (2013.01)

FIG. 5

# PEG-ACS/M-SIRNA NANOCOMPOSITE, APPLICATION THEREOF, AND METHOD FOR REDUCING HISTAMINE CONTENT DURING FISHMEAL STORAGE

CROSS REFERENCE TO RELATED APPLICATIONS

This application is based upon and claims priority to Chinese Patent Application No. 201810739772.5, filed on Jul. 6, 2018, the entire content of which is incorporated herein by reference.

SEQUENCE LISTING

The instant application contains a Sequence Listing which has been submitted in ASCII format via EFS-Web and is hereby incorporated by reference in its entirety. Said ASCII copy is named "GBHZLZ001. Sequence Listing1.txt" created on 10/21/2020 and is 3 KB in size.

TECHNICAL FIELD

The invention belongs to the field of the feed industry, and more specifically, to a method for preparing a PEG-ACS/M-siRNA nanocomposite and an application method thereof in fishmeal storage, aimed at reducing the histamine content in fishmeal storage and improving the feeding safety of fishmeal.

BACKGROUND

Fishmeal is a powder obtained by way of processing the whole fish or fish waste as raw materials via steaming, pressing, dehydrating, degreasing, drying, crushing and the like. As a high-quality animal protein feedstuff, fishmeal has a crude protein content of more than 55% and is rich in essential amino acids, essential fatty acids, minerals and vitamins. In addition, fishmeal also contains a large number of "unknown growth factors" which can promote animal growth, thus playing an important role in feed production. However, during the process of storage, the abundant histidine in the fishmeal undergoes decarboxylation under the action of histidine decarboxylase to form histamine, which is highly toxic to animals. Studies show that *Morganella morganii* has a high histidine decarboxylase activity and is the main spoilage species for the formation of histamine in fishmeal. Therefore, the inhibition of the expression of histidine decarboxylase of *Morganella morganii* is an effective way to inhibit the formation of histamine in fishmeal.

Histamine, as a biogenic amine, can interact with receptors on the cell membrane and thus cause histamine poisoning. The derivative of histamine called gizzerosine has 100 times the pathogenic ability than that of histamine. It is reported that 2.2 mg/kg of gizzerosine can stimulate the gastric acid secretion in poultry to cause stomach diseases and cause liver damage in fish. At present, the main methods for reducing histamine in fishmeal include irradiation, as well as the improvement of processing and storage conditions. These methods have the disadvantages of high operation requirements, high cost and ineffective effects, and are difficult to apply and popularize in production. Therefore, an efficient, simple, practical and safe method to reduce the histamine content in fishmeal has important significance for the feed industry.

The RNA interference technology is to block the gene activity of a target-specific gene by homologous double-stranded RNA (dsRNA). According to the principle of base pairing, small-interfering RNA (siRNA) has a high specificity, only interferes with target genes and does not work for other sequences. At present, non-viral vectors of siRNA are mainly cationic liposomes and cationic polymers, such as polyethyleneimine and chitosan. However, both liposome and polyethyleneimine have a high cytotoxicity and toxicity in vivo, while chitosan as a carrier has low efficiency and poor targeting.

In the present invention, the modified chitosan is chosen to be a siRNA transferring carrier in the constructed PEG-ACS/M-siRNA nanocomposite, which can silence the histidine decarboxylase of the main histamine-producing microorganism *Morganella morganii* by specifically combining with its mRNA according to the principle of base pairing, thereby inhibiting the synthesis of histamine in fishmeal, effectively delaying the decay process of fishmeal during storage, and having broad application prospects.

SUMMARY

The objective of the present invention is to provide a preparation method of a PEG-ACS/M-siRNA nanocomposite and application strategies. By inhibiting the expression of histidine decarboxylase gene of the main histamine-producing microorganism in fishmeal *Morganella morganii*, the content of histamine in fishmeal during storage is reduced. Aimed at ensuring the quality and safety of the fishmeal, an efficient and easy method for reducing the histamine content is provided.

The present invention adopts the following technical solution:

The present invention provides a PEG-ACS/M-siRNA nanocomposite, wherein the M-siRNA is designed according to the histidine decarboxylase gene (MU9_RS17900 Gene ID: 14672734) sequence (SEQ NO: 1) of *Morganella morganii* (*Morganella morganii* subsp. *morganii* KT) (CP004345), and the PEG-ACS/M-siRNA nanocomposite is prepared by using the PEGylated arginine-modified chitosan as a carrier.

Furthermore, the M-siRNA is double-stranded, the sequence of which is selected from the following sequences:

```
(1) positive-sense strand:
                                      (SEQ NO: 2)
    5'-GGAUCGUAUUUCUGUUGAAAU-3', antisense strand:
                                      (SEQ NO: 3)
    5'-UUCAACAGAAAUACGAUCCAC-3';

(2) positive-sense strand:
                                      (SEQ NO: 4)
    5'-GUAUUUCUGUUGAAAUCGACU-3', antisense strand:
                                      (SEQ NO: 5)
    5'-UCGAUUUCAACAGAAAUACGA-3';

(3) positive-sense strand:
                                      (SEQ NO: 6)
    5'-GUAUCAAACGUGAAGAUUACU-3', antisense strand:
                                      (SEQ NO: 7)
    5'-UAAUCUUCACGUUUGAUACCG-3'.
```

Furthermore, the PEGylated arginine-modified chitosan is prepared by the following steps:

(1) preparation of arginine-modified chitosan: the chitosan is dissolved in a TEMED/HCl buffer solution, and then the 1-ethyl-3 (3-dimethylaminopropyl) carbodiimide and N-hydroxyl-succinimide coupling agents are added to the solution; after being stirred evenly, the arginine containing chitosan amino with a molar amount of 50%-100% is added, reacting under a magnetic stirring for 6-10 h at room temperature, and then dialyzed with demineralized water and freeze-dried to obtain the arginine-modified chitosan;

(2) preparation of PEG-ACS: the arginine-modified chitosan is taken, added with PEG-SPA, reacting at room temperature and dialyzed with a dialysis bag with a molecular weight cutoff of 14,000, and the PEGylated arginine-modified chitosan is obtained after the unreacted PEG is removed.

Furthermore, in Step (1), 1-ethyl-3 (3-dimethylaminopropyl) carbodiimide and chitosan are equimolar, and the N-hydroxy-succinimide coupling agent and chitosan are equimolar.

Furthermore, the preparation of the PEG-ACS/M-siRNA composite comprises the following steps of:

(a) preparing the siRNA solution: siRNA is dissolved in the DEPC water to prepare an siRNA solution at a concentration of 18-25 μM;

(b) dissolving PEG-ACS in the NaAc/HAc buffer solution, respectively incubated with the siRNA solution in a constant temperature water bath at 50-55° C. for 10-15 min, then mixing the two solutions in an equal volume and quickly mixing them in a vortex mixer for 30-40 s to obtain the PEG-ACS/M-siRNA nanoparticle.

The particle size of the PEG-ACS/M-siRNA nanocomposite is 150-250 nm.

Furthermore, the specific preparation method of the PEG-ACS/M-siRNA nanocomposite is as follows:

(1) the M-siRNA sequence is designed according to the target sequence 5'-GTGGATCGTATTTCTGTTGAAAT-3' (SEQ NO: 8) of the histidine decarboxylase gene MU9 RSI7900 in the main histamine-producing microorganism *Morganella morganii* in fishmeal.

(2) Preparation of M-siRNA sequence:

```
Positive-sense strand:
                                  (SEQ NO: 2)
5'-GGAUCGUAUUUCUGUUGAAAU-3', antisense strand:
                                  (SEQ NO: 3)
5'-UUCAACAGAAAUACGAUCCAC-3'.
```

(3) Preparation of arginine-modified chitosan (ACS): 0.5-1.5 g of chitosan is dissolved in the N, N, N', N'-tetramethylethylenediamine (pH 4.5-5.0) (TEMED)/hydrochloric acid buffer solution, then added with 1-ethyl-3 (3-dimethylaminopropyl) carbodiimide (EDC) and N-hydroxyl-succinimide (NHS) having an equimolar amount with the chitosan amino as a coupling agent. After being stirred evenly, the arginine containing chitosan amino with a molar amount of 50%-100% is added, reacting under a magnetic stirring for 6-10 h at room temperature, and dialyzed with demineralized water and freeze-dried to obtain the arginine-modified chitosan.

(4) Preparation of PEGylated arginine-modified chitosan (PEG-ACS): 2.5 mL of 10 mg/mL arginine-modified chitosan is taken and added with 25 mg of PEG-SPA to react at room temperature for 4-5 h. The PEGylated arginine-modified chitosan is obtained after the unreacted PEG is removed through dialysis using a molecular weight cutoff of 14,000, and then is freeze-dried for use.

(5) Preparation of siRNA solution: siRNA is dissolved in the DEPC water to prepare the siRNA solution at a concentration of 18-25 μM and stored at −20° C. for use. The siRNA should not be frozen-thawed for more than 5 times.

(6) Preparation of PEG-ACS/M-siRNA nanocomposite: the PEG-ACS/M-siRNA nanocomposite is prepared by a complex coacervation. PEG-ACS is dissolved in the NaAc/HAc buffer solution (pH 5.5) to a mass fraction of 0.02%. The PEG-ACS solution and the siRNA solution are incubated in a constant temperature water bath at 50-55° C. for 10-15 min, respectively, then mixed in an equal volume, and quickly mixed in a vortex mixer for 30-40 s to obtain the PEG-ACS/M-siRNA nanoparticle.

(7) The particle size of the nanocomposite is measured by dynamic light scattering between 150-250 nm. The prepared composite is frozen at −20° C. for 3-6 h and then freeze-dried for 20-26 h to obtain the lyophilized powder for use.

In use, the PEG-ACS/M-siRNA lyophilized powder is added to the fishmeal in a certain ratio.

Preferably, the chitosan described in Step (3) has a molecular weight of $5 \times 10^4$ D and a degree of deacetylation of 82%.

Preferably, the amount of the coupling agent described in Step (3) is an equimolar amount of chitosan amino.

Preferably, the amount of arginine described in Step (3) is 50%-100% of the molar amount of chitosan amino.

Preferably, the mass ratio of ACS to PEG-SPA described in Step (4) is 1:1.

Preferably, the dialysis bag described in Step (4) has a molecular weight of 14,000.

Preferably, the water bath temperature in Step (6) is 50-55° C. for 10-15 min.

Preferably, the PEG-ACS solution described in Step (6) is mixed with an equal volume of the siRNA solution.

Preferably, the PEG-ACS/M-siRNA nanocomposite described in Step (7) has a particle diameter of 150-250 nm.

Preferably, the freezing time described in Step (7) is 4 h and the freeze-drying time is 24 h.

The invention also provides the application of the above PEG-ACS/M-siRNA nanocomposite in the fishmeal storage.

Furthermore, 3-6 g of PEG-ACS/M-siRNA nanocomposite is added per kilogram of fishmeal.

The invention also provides a method for reducing the histamine content in the fishmeal storage, wherein the above PEG-ACS/M-siRNA nanocomposite is added to the fishmeal, and the addition ratio is 3-6 g of PEG-ACS/M-siRNA nanocomposite per kilogram of fishmeal.

Compared with the prior art, the advantages of the present invention are as follows:

The invention prepares a PEG-ACS/M-siRNA nanocomposite using modified chitosan as a siRNA carrier for reducing the histamine synthesis in the fishmeal storage. The expression of the histidine decarboxylase gene is inhibited by PEG-ACS/M-siRNA nanocomposites via specifically binding with the mRNA of histidine decarboxylase gene of *Morganella morganii*, and fundamentally inhibiting the synthesis of histamine, effectively delaying the decay process of fishmeal during the process of storage, and having broad application prospects.

It is proved that the PEG-ACS/M-siRNA nanocomposite is characterized by high efficiency and strong targeting. The method of the present invention has a significant effect on the reduction of histamine content in fishmeal. Compared with the control group, the histamine content decreases significantly by 49%-53%, which can effectively extend the shelf life of fishmeal.

DETAILED DESCRIPTION OF THE EMBODIMENTS

The technical solutions of the present invention will be fully described below in conjunction with specific embodiments. In the embodiments of the present invention, different amounts of PEG-ACS/M-siRNA nanocomposite are added to the fishmeal, and the histamine content of the product is significantly reduced by 49%-53%.

Embodiment 1

(1) Design of M-siRNA sequence.

```
Positive-sense strand:
                                       (SEQ NO: 2)
5'-GGAUCGUAUUUCUGUUGAAAU-3', antisense strand:
                                       (SEQ NO: 3)
5'-UUCAACAGAAAUACGAUCCAC-3'.
```

(2) Preparation of M-siRNA.

(3) Preparation of ACS: 0.5 g of chitosan is weighed and dissolved in a TEMED/HCl buffer solution (pH 5.0), and then 567 mg of EDC and 340 mg of NHS coupling agents are added to the solution; after being stirred evenly, the arginine containing chitosan amino with a molar amount of 80% is added, reacting under a magnetic stirring for 8 h at room temperature, and then dialyzed with demineralized water and freeze-dried to obtain the arginine-modified chitosan.

(4) Preparation of PEG-ACS: 2.5 mL of 10 mg/mL arginine-modified chitosan is taken and added with 25 mg of PEG-SPA to react at room temperature for 4 h. The PEGylated arginine-modified chitosan is obtained after the unreacted PEG is removed through dialysis using a molecular weight cutoff of 14,000, and then is freeze-dried for use.

(5) Preparation of siRNA solution: siRNA is dissolved in the DEPC water to prepare the siRNA solution at a concentration of 20 μM and stored at −20° C. for use.

(6) Preparation of PEG-ACS/M-siRNA: PEG-ACS is dissolved in the NaAc/HAc buffer solution (pH 5.5) to a mass fraction of 0.02%. The PEG-ACS solution and the siRNA solution are respectively incubated in a constant temperature water bath at 50° C. for 10 min, then mixed in an equal volume, and quickly mixed in a vortex mixer for 30 s to obtain the PEG-ACS/M-siRNA nanocomposite.

(7) The average particle size of the nanocomposite is measured by a dynamic light scattering method to be 217 nm. The prepared composite is frozen at −20° C. for 4 h and then freeze-dried for 24 h to obtain the lyophilized powder for use.

(8) 5.5 g of PEG-ACS/M-siRNA nanocomposite per kilogram of fishmeal is added.

(9) High-performance liquid chromatography (HPLC) is used to detect the histamine content in the fishmeal, and a blank control is performed. The results are shown in Table 1 and FIG. 1.

TABLE 1

Histamine content in the fishmeal under different treatments (mg/100 g)

| | Storage time/month | | | | | |
|---|---|---|---|---|---|---|
| | January | February | March | April | May | June |
| Control group | 43.64 | 47.52 | 52.08 | 58.01 | 65.24 | 76.83 |
| Treatment group | 20.43 | 22.56 | 24.98 | 27.78 | 31.58 | 36.81 |

| | Storage time/month | | | | | |
|---|---|---|---|---|---|---|
| | July | August | September | October | November | December |
| Control group | 93.97 | 109.52 | 121.29 | 129.73 | 134.67 | 138.75 |
| Treatment group | 45.72 | 53.25 | 58.49 | 62.37 | 65.55 | 67.71 |

As shown in Table 1, during the process of storage, the histamine content in the fishmeal increased continuously, and the standard of feed deterioration was achieved in August (the amine content of the secondary fishmeal was ≤1000 mg/kg). The fishmeal added with PEG-ACS/M-siRNA nanocomposite did not reach the deterioration standard even in December, and the experimental results showed that the fishmeal could be effectively extended. Combined with the results, a further comparative analysis showed that the inhibition of histamine in fishmeal by the PEG-ACS/M-siRNA nanocomposite reached 51%-53%.

Figure 1:
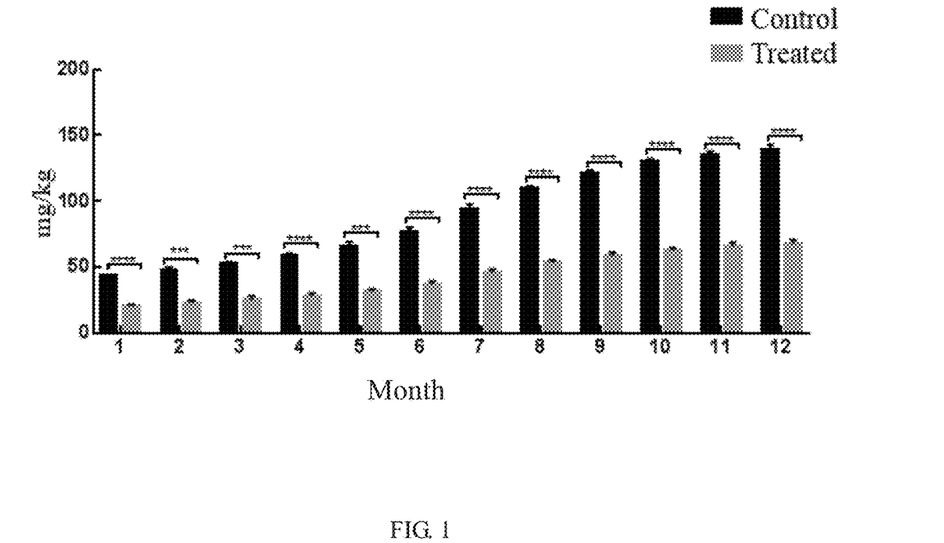
FIG. 1 shows the histamine content in fishmeal under different treatments in Embodiment 1.

As shown in FIG. 1, during the process of storage, the histamine content in the fishmeal increased, and the PEG-ACS/M-siRNA nanocomposite significantly reduced the histamine content in the fishmeal in February, March, and May and significantly reduced the histamine content in the fishmeal in other months. The PEG-ACS/M-siRNA nanocomposite has obvious inhibitory effects on the histamine synthesis during the process of fishmeal storage.

Figure 3:
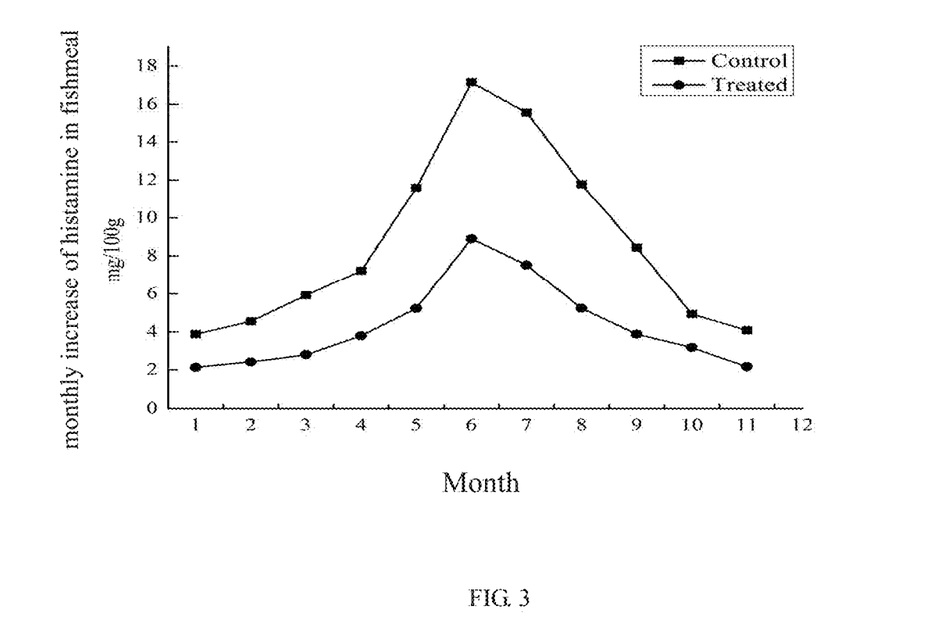
FIG. 3 shows the monthly increase of histamine in fishmeal under different treatments in Embodiment 1.

As shown in FIG. 3, during the process of storage, the histamine content in the fishmeal increased, and the amount of histamine was relatively increased in July and August. The PEG-ACS/M-siRNA nanocomposite has obvious inhibitory effects on the histamine synthesis during the process of fishmeal storage.

Embodiment 2

(1) Design of M-siRNA sequence.

```
Positive-sense strand:
                                       (SEQ NO: 2)
5'-GGAUCGUAUUUCUGUUGAAAU-3', antisense strand:
                                       (SEQ NO: 3)
5'-UUCAACAGAAAUACGAUCCAC-3'.
```

(2) Preparation of M-siRNA.

(3) Preparation of ACS: 0.8 g of chitosan is weighed and dissolved in a TEMED/HCl buffer solution (pH 4.5), and then 900 mg of EDC and 550 mg of NHS coupling agent are added to the solution; after being stirred evenly, the arginine containing chitosan amino with a molar amount of 100% is added, reacting under a magnetic stirring for 7 h at room temperature, and then dialyzed with demineralized water and freeze-dried to obtain the arginine-modified chitosan.

(4) Preparation of PEG-ACS: 3 mL of 8 mg/mL arginine-modified chitosan is taken and added with 24 mg of PEG-SPA to react at room temperature for 4 h. The PEGylated arginine-modified chitosan is obtained after the unreacted PEG is removed through dialysis using a molecular weight cutoff of 14,000, and then is freeze-dried for use.

(5) Preparation of siRNA solution: siRNA is dissolved in the DEPC water to prepare the siRNA solution at a concentration of 18 μM and stored at −20° C. for use.

(6) Preparation of PEG-ACS/M-siRNA: PEG-ACS is dissolved in the NaAc/HAc buffer solution (pH 5.5) to a mass fraction of 0.02%. The PEG-ACS solution and the siRNA solution are respectively incubated in a constant temperature water bath at 55° C. for 15 min, then mixed in an equal volume, and quickly mixed in a vortex mixer for 40 s to obtain the PEG-ACS/M-siRNA nanocomposite.

(7) The average particle size of the nanocomposite is measured by a dynamic light scattering method to be 215 nm. The prepared composite is frozen at −20° C. for 5 h and then freeze-dried for 20 h to obtain the lyophilized powder for use.

(8) 4 g of PEG-ACS/M-siRNA nanocomposite per kilogram of fishmeal is added.

(9) High-performance liquid chromatography (HPLC) is used to detect the histamine content in the fishmeal, and a blank control is performed. As shown in Table 2 and FIG. 2, the inhibition of the histamine in the fishmeal storage by PEG-ACS/M-siRNA nanocomposite is about 49%-51%.

TABLE 2

Histamine content in fishmeal under different treatments (mg/100 g)

| | Storage time/month | | | | | |
|---|---|---|---|---|---|---|
| | January | February | March | April | May | June |
| Control group | 44.68 | 48.81 | 53.5 | 59.51 | 67.03 | 79.42 |
| Treatment group | 22.17 | 24.28 | 26.64 | 29.75 | 33.89 | 39.53 |

| | Storage time/month | | | | | |
|---|---|---|---|---|---|---|
| | July | August | September | October | November | December |
| Control group | 97.53 | 113.82 | 126.05 | 134.81 | 139.64 | 143.89 |
| Treatment group | 48.39 | 55.89 | 61.75 | 65.66 | 68.93 | 71.02 |

As shown in Table 2, during the process of storage, the histamine content in the fishmeal increased continuously, and the standard of feed deterioration was achieved in August (the amine content of the secondary fishmeal was ≤1000 mg/kg). The fishmeal added with PEG-ACS/M-siRNA nanocomposite did not reach the deterioration standard even in December, and the experimental results showed that the fishmeal could be effectively extended. Combined with the results, a further comparative analysis showed that the inhibition of histamine in fishmeal by the PEG-ACS/M-siRNA nanocomposite reached 49%-51%.

Figure 2:
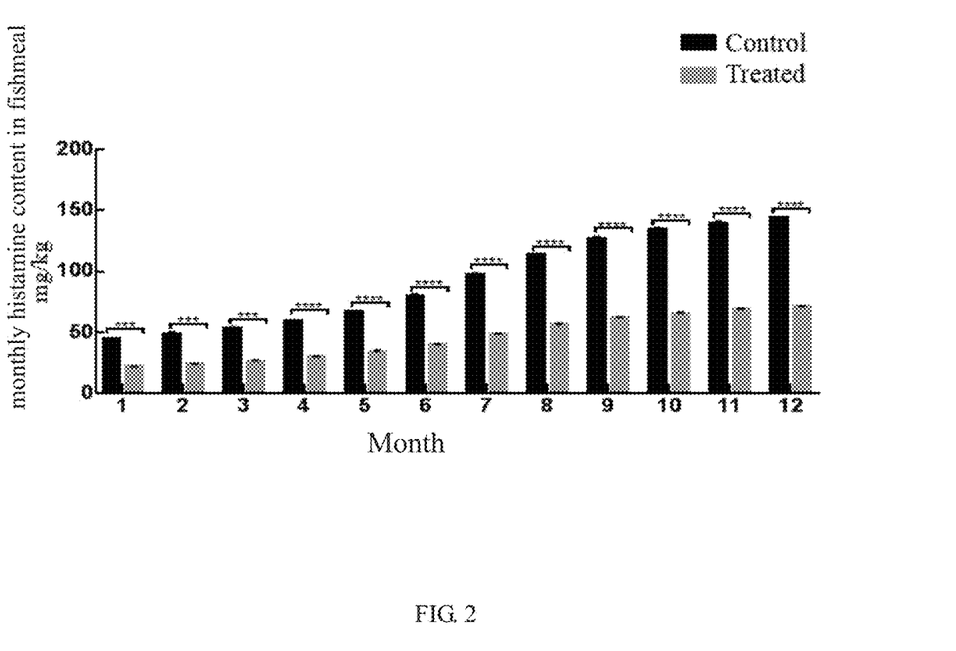
FIG. 2 shows the histamine content in fishmeal under different treatments in Embodiment 2.

As shown in FIG. 2, during the process of storage, the histamine content in the fishmeal increased, and the PEG-ACS/M-siRNA nanocomposite significantly reduced the histamine content in the fishmeal in January, February and March and significantly reduced the histamine content in the fishmeal in other months. The PEG-ACS/M-siRNA nanocomposite has obvious inhibitory effects on the histamine synthesis during the process of fishmeal storage.

Figure 4:
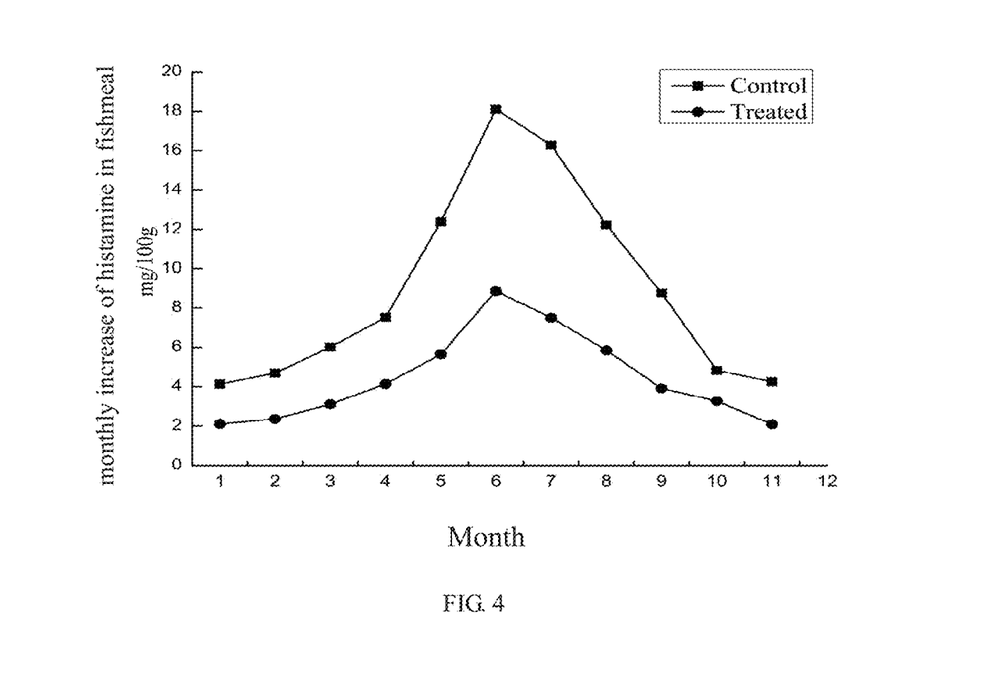
FIG. 4 shows the monthly increase of histamine in fishmeal under different treatments in Embodiment 2.

As shown in FIG. 4, during the process of storage, the histamine content in the fishmeal increased, and the amount of histamine was relatively increased in July and August. The PEG-ACS/M-siRNA nanocomposite has obvious inhibitory effects on the histamine synthesis during the process of fishmeal storage.

Comparative Example 1

Experimental steps using chitosan as a carrier:
(1) Design of M-siRNA sequence.
(2) Preparation of M-siRNA.
(3) Preparation of CS solution: CS is dissolved in NaAc/HAc buffer solution (pH=4.5) to obtain 1 mg/mL of CS solution, and the pH is adjusted to 5.5 with a NaOH solution.
(5) Preparation of siRNA solution: siRNA is dissolved in the DEPC water to prepare the siRNA solution at a concentration of 18-25 LM and stored at −20° C. for use.
(4) Preparation of CS/M-siRNA nanocomposite: the CS solution and the si RNA solution are respectively incubated in a constant temperature water bath at 50-55° C. for 10-15 min, then mixed in an equal volume, and quickly mixed in a vortex mixer for 30-40 s to obtain the CS/M-siRNA nanoparticle.
(5) The particle size of the nanocomposite is measured by a dynamic light scattering method between 170-240 nm. The prepared composite is frozen at −20° C. for 3-6 h and then freeze-dried for 20-26 h to obtain the lyophilized powder for use.
(6) The CS/M-siRNA freeze-dried powder is added to fishmeal at a ratio of 3.5-5 g of nanocomposite per kilogram of fishmeal.

Figure 5:
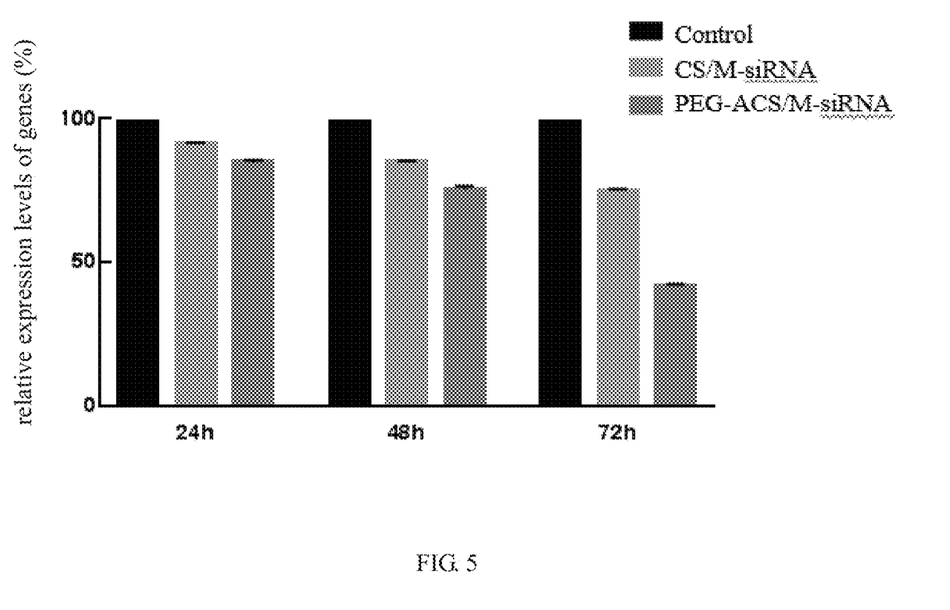
FIG. 5 shows the changes in the expression level of the histidine decarboxylase gene with time using different siRNA carriers in Comparative Example 1 and Embodiment 1.

As shown in FIG. 5, when the chitosan is used as a carrier for transmitting siRNA, the expression of histidine decarboxylase can be reduced to some extent, but it has disadvantages such as inefficiency and poor targeting. When the PEGylated arginine-modified chitosan is used as a carrier for transmitting siRNA, the expression level of histidine decarboxylase is significantly decreased. The PEG-ACS/M-siRNA nanocomposite shows a high efficiency and strong targeting.

What is claimed is:

1. A PEGylated arginine-modified chitosan/small-interfering RNA (PEG-ACS/siRNA) nanocomposite, comprising a small-interfering RNA (siRNA), wherein the siRNA is designed according to a histidine decarboxylase gene of *Morganella morganii* (*Morganella morganii* subsp. *morganii* KT); and the histidine decarboxylase gene has the sequence of SEQ ID No: 1; and the PEG-ACS/siRNA nanocomposite is prepared by using a PEGylated arginine-modified chitosan (PEG-ACS) as a carrier.

2. The PEG-ACS/siRNA nanocomposite of claim 1, wherein the siRNA is double-stranded and comprises the sequence of:
   positive-sense strand: SEQ ID No: 2,
   antisense strand: SEQ ID No: 3.

3. The PEG-ACS/siRNA nanocomposite of claim 1, wherein the *PEG-ACS/siRNA nanocomposite has a particle diameter of 150-250 nm.

4. A method for storing fishmeal, comprising: administering a PEG-ACS/small-interfering RNA (siRNA) nanocomposite to store the fishmeal; wherein the PEG-ACS/siRNA nanocomposite comprises a siRNA; and wherein the siRNA is designed according to a histidine decarboxylase gene of *Morganella morganii* (*Morganella morganii* subsp. *morganii* KT); and the histidine decarboxylase gene has the sequence of SEQ ID No: 1; and the *PEG-ACS/siRNA nanocomposite is prepared by using a PEGylated arginine-modified chitosan as a carrier.

5. The method of claim 4, wherein 3-6 g of the PEG-ACS/siRNA nanocomposite is added per kilogram of the fishmeal.

6. A method for reducing a histamine content in fishmeal storage, wherein a PEG-ACS/small-interfering RNA (siRNA) nanocomposite is added to the fishmeal storage, wherein a PEG-ACS/siRNA nanocomposite is added to the fishmeal, at an addition ratio of 3-6 g of the PEG-ACS/siRNA nanocomposite per kilogram of the fishmeal; wherein the PEG-ACS/siRNA nanocomposite nanocomposite comprises a siRNA; and wherein the siRNA is designed according to a histidine decarboxylase gene of *Morganella morganii* (*Morganella morganii* subsp. *morganii* KT); and the histidine decarboxylase gene has the sequence of SEQ ID No: 1; and the PEG-ACS/siRNA nanocomposite is prepared by using a PEGylated arginine-modified chitosan as a carrier.

7. The method of claim 4, wherein the siRNA is double-stranded and comprises the sequence of:
   positive-sense strand: SEQ ID No: 2, antisense strand: SEQ ID No: 3.

8. The method of claim 4, wherein the PEGylated arginine-modified chitosan is prepared by the following steps:

(1) preparation of an arginine-modified chitosan: dissolving a chitosan in a TEMED/HCl buffer solution to obtain a first solution, and then adding a 1-ethyl-3(3-dimethylaminopropyl) carbodiimide and a N-hydroxyl-succinimide coupling agent to the first solution to obtain a second solution; stirring the second solution evenly to obtain a third solution, adding an arginine containing chitosan amino with a molar amount of 50%-100% to the third solution to obtain a fourth solution, reacting the fourth solution under a magnetic stirring for 6-10 h at room temperature to obtain a fifth solution, and then dialyzing the fifth solution with demineralized water to obtain a sixth solution, and freeze-drying the sixth solution to obtain the arginine-modified chitosan;

(2) preparation of the PEG-ACS: taking the arginine-modified chitosan, adding a PEG-SPA, reacting at room temperature and dialyzing with a dialysis bag with a molecular weight cutoff of 14,000, and removing an untreated PEG to obtain the PEGylated arginine-modified chitosan.

9. The method of claim 8, wherein the 1-ethyl-3 (3-dimethylaminopropyl) carbodiimide and the chitosan are equimolar, and the N-hydroxy-succinimide coupling agent and the chitosan are equimolar.

10. The method of claim 4, wherein the preparation of the PEG-ACS/siRNA nanocomposite comprises the following steps:
    (a) preparation of a siRNA solution: dissolving the siRNA in DEPC water to prepare the siRNA solution at a concentration of 18-25 µM;
    (b) dissolving the PEG-ACS in a NaAc/HAc buffer solution to obtain a solution, incubating the solution and the siRNA solution at a constant temperature water bath at 50-55° C. for 10-15 min respectively, then quickly mixing the solution and the siRNA solution in an equal volume in a vortex mixer for 30-40 s to obtain the PEG ACS/siRNA nanocomposite.

11. The method of claim 4, wherein the PEG ACS/siRNA nanocomposite has a particle diameter of 150-250 nm.

12. The method of claim 6, wherein the siRNA is double-stranded and comprises the sequence of:
    positive-sense strand: SEQ ID No: 2, antisense strand: SEQ ID No: 3.

13. The method of claim 6, wherein the PEGylated arginine-modified chitosan is prepared by the following steps:
    preparation of an arginine-modified chitosan: dissolving a chitosan in a TENTED/HCl buffer solution to obtain a first solution, and then adding a 1-ethyl-3(3-dimethylaminopropyl) carbodiimide and a N-hydroxyl-succinimide coupling agent to the first solution; to obtain a second solution, adding an arginine containing chitosan amino with a molar amount of 50%-100% to the second solution to obtain a third solution, reacting the third solution under a magnetic stirring for 6-10 h at room temperature, and then dialyzing with demineralized water, and freeze drying to obtain the arginine-modified chitosan;

(2) preparation of the PEG-ACS: taking the arginine-modified chitosan, adding a PEG SPA, reacting at room temperature and dialyzing with a dialysis bag with a molecular weight cutoff of 14,000, and removing an untreated PEG to obtain the PEGylated arginine-modified chitosan.

14. The method of claim 13, wherein the 1-ethyl-3(3-dimethylaminopropyl) carbodiimide and the chitosan are equimolar, and the N-hydroxy-succinimide coupling agent and the chitosan are equimolar.

15. The method of claim 6, wherein the preparation of the PEG-ACS/siRNA nanocomposite comprises the following steps:
    (a) preparation of a siRNA solution: dissolving the siRNA in DEPC water to prepare the siRNA solution at a concentration of 18-25 µM;
    (b) dissolving the PEG-ACS in a NaAc/HAc buffer solution to obtain a solution, incubating the solution and the siRNA solution at a constant temperature water bath at 50-55° C. for 10-15 min respectively, then quickly mixing the solution and the siRNA solution in an equal volume in a vortex mixer for 30-40 s to obtain the PEG ACS/siRNA nanocomposite.

16. The method of claim 6, wherein the PEG ACS/siRNA nanocomposite has a particle diameter of 150-250 nm.

17. The PEG-ACS/siRNA nanocomposite of claim 1, wherein the siRNA is double-stranded and comprises the sequence of:
    positive-sense strand: SEQ ID No: 4, antisense strand: SEQ ID No: 5.

18. The PEG-ACS/siRNA nanocomposite of claim 1, wherein the siRNA is double-stranded and comprises the sequence of:
    positive-sense strand: SEQ ID No: 6, antisense strand: SEQ ID No: 7.

19. The method of claim 4, wherein the siRNA is double-stranded and comprises the sequence of:
    positive-sense strand: SEQ ID No: 4, antisense strand: SEQ ID No: 5.

20. The method of claim 4, wherein the siRNA is double-stranded and comprises the sequence of:
    positive-sense strand: SEQ ID No: 6, antisense strand: SEQ ID No: 7.

* * * * *

SEQUENCE LISTING

<160> NUMBER OF SEQ ID NOS: 8

<210> SEQ ID NO 1
<211> LENGTH: 1137
<212> TYPE: DNA
<213> ORGANISM: Morganella morganii subsp. morganii KT

```
<400> SEQUENCE: 1
atgactctgt ctatcaatga tcaaaacaaa cttgatgcat tctgggctta ttgcgtaaaa        60
aaccagtatt tcaacatcgg ctatcctgaa tcagcggatt tcgattacac caacctggaa       120
cgtttcttac gtttctccat caacaactgc ggtgactggg gcgaatattg caactacctg       180
ctgaactctt tcgatttcga gaaagaagtg atggagtatt tcgcagacct gttcaaaatt       240
ccgtttgaac aaagctgggg ttatgtgacc aacggcggta ctgaaggtaa catgttcggt       300
tgctacctgg ccgtgaaat cttccctgac ggtaccctgt actattcaaa agatactcac        360
tattccgttg cgaaaatcgt taaattactg cgtatcaaat ctcaggttgt tgaatctctg       420
ccaaacggcg aaatcgacta tgacgatctg atgaaaaaaa tcgctgacga taaagaagcg       480
catccgatca ttttcgctaa catcggtacc actgtccgcg gtgctattga tgatatcgct       540
gaaatccaga aacgcctgaa agcagccggt atcaaacgtg aagattacta cctgcacgct       600
gatgcggcac tgagcggcat gatcctgcca ttcgttgatg atgcacagcc attcacgttt       660
gctgacggta tcgactcaat cggtgttttcc ggccataaaa tgattggttc gccaatccct       720
tgcggtatcg ttgttgcgaa gaaagaaaac gtggatcgta tttctgttga aatcgactac       780
atctccgcac acgacaaaac catcaccggt tcacgtaacg gtcacacacc actgatgctg       840
tgggaagcta tccgttcaca ttcaactgag gaatggaaac gccgcatcac ccgcagtctg       900
gatatggctc agtacgctgt tgaccgtatg cagaaagccg gtatcaatgc atggcgcaac       960
aaaaactcca tcactgttgt gttccctttgc ccgtcagaac gcgtctggag agaacattgc      1020
ctggcaacgt ccggcgacgt ggctcacctg atcaccaccg cgcaccatct ggataccgcg      1080
cagatcgaca aactgatcga cgacgttatc gcggatttta acttacacgc ggcataa         1137

<210> SEQ ID NO 2
<211> LENGTH: 21
<212> TYPE: RNA
<213> ORGANISM: Artificial Sequence
<220> FEATURE:
<223> OTHER INFORMATION: The sequence is synthesized

<400> SEQUENCE: 2
ggaucguauu ucuguugaaa u                                                  21

<210> SEQ ID NO 3
<211> LENGTH: 21
<212> TYPE: RNA
<213> ORGANISM: Artificial Sequence
<220> FEATURE:
<223> OTHER INFORMATION: The sequence is synthesized

<400> SEQUENCE: 3
uucaacagaa auacgaucca c                                                  21

<210> SEQ ID NO 4
<211> LENGTH: 21
<212> TYPE: RNA
<213> ORGANISM: Artificial Sequence
<220> FEATURE:
<223> OTHER INFORMATION: The sequence is synthesized

<400> SEQUENCE: 4
guauuucugu ugaaaucgac u                                                  21

<210> SEQ ID NO 5
```

```
<211> LENGTH: 21
<212> TYPE: RNA
<213> ORGANISM: Artificial Sequence
<220> FEATURE:
<223> OTHER INFORMATION: The sequence is synthesized

<400> SEQUENCE: 5
ucgauuucaa cagaaauacg a                                              21

<210> SEQ ID NO 6
<211> LENGTH: 21
<212> TYPE: RNA
<213> ORGANISM: Artificial Sequence
<220> FEATURE:
<223> OTHER INFORMATION: The sequence is synthesized

<400> SEQUENCE: 6
guaucaaacg ugaagauuac u                                              21

<210> SEQ ID NO 7
<211> LENGTH: 21
<212> TYPE: RNA
<213> ORGANISM: Artificial Sequence
<220> FEATURE:
<223> OTHER INFORMATION: The sequence is synthesized

<400> SEQUENCE: 7
uaaucuucac guuugauacc g                                              21

<210> SEQ ID NO 8
<211> LENGTH: 23
<212> TYPE: DNA
<213> ORGANISM: Artificial sequence
<220> FEATURE:
<223> OTHER INFORMATION: target sequence of the histidine decarboxylase
      gene

<400> SEQUENCE: 8
gtggatcgta tttctgttga aat                                            23
```